United States Patent [19]

Jakkula et al.

[11] Patent Number: 5,315,258
[45] Date of Patent: May 24, 1994

[54] METHOD AND APPARATUS FOR DETERMINING THE MOISTURE CONTENT OF A MATERIAL

[75] Inventors: Pekka Jakkula, Oulu; Esko Tahkola, Kiviniemi, both of Finland

[73] Assignee: Kajaani Elektroniikka Oy, Kajaani, Finland

[21] Appl. No.: 859,893

[22] Filed: Mar. 30, 1992

Related U.S. Application Data

[63] Continuation-in-part of Ser. No. 464,281, Jan. 12, 1990, abandoned.

[30] Foreign Application Priority Data

Jan. 13, 1989 [FI]  Finland ................................. 890201

[51] Int. Cl.$^5$ ...................... G01R 27/04; G01R 25/04
[52] U.S. Cl. ..................... 324/640; 324/643; 324/634; 342/122
[58] Field of Search ............ 324/634, 640, 643, 639, 324/642

[56] References Cited

U.S. PATENT DOCUMENTS

| | | |
|---|---|---|
| 3,599,088 | 8/1971 | Busker . |
| 3,851,244 | 11/1974 | Mounce . |
| 4,123,702 | 10/1978 | Kinanen .............................. 324/639 |
| 4,135,131 | 1/1979 | Larsen ................................ 324/639 |
| 4,155,035 | 5/1979 | Fitzky ................................. 324/636 |
| 4,297,874 | 11/1981 | Sasaki . |
| 4,361,801 | 11/1982 | Meyer . |
| 4,546,311 | 10/1985 | Knochel . |
| 4,675,595 | 6/1987 | Hane . |
| 4,727,311 | 2/1988 | Walker . |

FOREIGN PATENT DOCUMENTS 1130863 8/1982 Canada .
2239848 2/1974 Fed. Rep. of Germany .

OTHER PUBLICATIONS

Skol-Nik: "Introduction To Radar Systems"-McGraw Hill—1980—pp. 81-85 (no month).

Primary Examiner—Kenneth A. Wieder
Assistant Examiner—Jose M. Solis
Attorney, Agent, or Firm—Kane, Dalsimer, Sullivan, Kurucz, Levy, Eisele and Richard

[57] ABSTRACT

In the method of the invention, a microwave signal is passed through a material whose moisture content is to be measured, the change in the velocity of the signal which has travelled through the material is measured and the moisture content is determined on the basis of the measured change and a known interdependence between the changes in the microwave signal velocity and the moisture content of the material. The apparatus comprises a transmitting device (1) which transmits a microwave signal through the material to be measured, and a detecting device (2) and a counting device (3) which measure the change of velocity of the signal transmitted through the material and determine the moisture content of the material on the basis of a known interdependence of the change of velocity of the microwave signal in question and change of moisture content of the material.

7 Claims, 4 Drawing Sheets

METHOD AND APPARATUS FOR DETERMINING THE MOISTURE CONTENT OF A MATERIAL

This is a continuation-in-part of copending application Ser. No. 07/464,281 filed on Jan. 12, 1990, now abandoned.

The present invention relates to a method and an apparatus for determining the moisture content of a material.

The measuring methods and equipment currently used for on-line determination of the moisture content of materials are generally based on the use of capacitance, conductance, neutron scattering, infrared radiation or microwave radiation.

Microwaves are radio waves in the frequency range 300 MHz ... 300 GHz. The action of microwave hygrometers is generally based on the measurement of transit attenuation or phase shift. Transit attenuation measurement is sensitive to interference from reflections, and phase shift measurement is technically difficult to perform, especially in the case of thick material layers where the phase shift may exceed 360°.

The object of the present invention is to achieve a method and an apparatus—in the first place for application in the wood and paper industry—for on-line determination of the moisture content of materials and to enable the measurement results to be utilized for real-time regulation of processes.

The characteristic features of the method and apparatus of the invention are as stated in claim 1.

In the method for determining the moisture content of a material a microwave signal is passed through the material to be measured, the change in the velocity of the signal which has travelled through the material in a constant measuring gap is measured and the moisture content of the material is determined on the basis of the measured change and a known interdependence between the changes in the microwave signal velocity and the moisture content of the material. The invention has the advantage that the moisture measurement can be performed very quickly and continuously, e.g. in the case of a moving stream of material. Thus, the measurement results can be used for real-time regulation of continuous processes.

The invention is based on the fact that the velocity of propagation of a microwave in a material depends on the dielectric properties of the material as shown by the following equation:

$$v = c/\sqrt{(\epsilon_r' + |\epsilon_r|)/2} \qquad (1)$$

where $|\epsilon_r| = \sqrt{\epsilon_r'^2 + \epsilon_r''^2}$ $\epsilon_r'$ = real part of the relative dielectric constant of the material
$\epsilon_r''$ = imaginary part of the relative dielectric constant of the material
c = light velocity The dielectric constant of water is large in comparison with the dielectric constants of most other materials, which is why the velocity of a microwave passing through a wet material decreases more than the velocity of a wave passing through a dry material. This makes it possible to measure the moisture content of the material with the aid of microwave velocity measurements.

The microwave transit time (t) in a material can be determined from the formula (2) below:

$$t = d/v = d/(c/\sqrt{(\epsilon_r' + |\epsilon_r|)/2}) \qquad (2)$$

where
d = distance travelled by the microwave in the material
v = velocity of the microwave in the material
$\epsilon_r'$ = real part of the relative dielectric constant of the material
$\epsilon_r$ = relative dielectric constant of the material The microwave transit time measurement is commonly used in radars to determine the distance between the transmitting antenna and a reflecting surface or a receiving antenna, and there are several commonly known techniques to measure the transit time or the relative changes of the transit time. The basic radar measurement situation is shown in FIG. 1.

Figure 1:
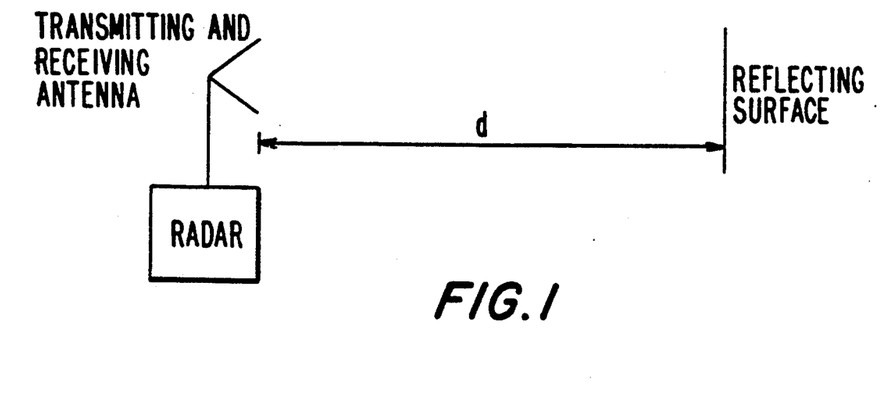
FIG. 1 illustrates a basic radar measurement setup.

Now in the setup of FIG. 1, when reflected signal is used the microwave transit time t is given by formula (3):

$$t = 2d/c \qquad (3)$$

where
d = distance between the transmitting antenna and the reflecting surface
c = the microwave velocity in air (the velocity of light)

The distance d can be determined from (3) because the microwave velocity in air is constant (the velocity of light) and the transit time t is measured. Different techniques to measure the distance by measuring the microwave transit time or the relative changes of it are well documented e.g. in Skolnik, M. I.:Introduction to Radar Systems, 2nd Ed., New York. MacGraw-Hill 1980/.

Figure 2:
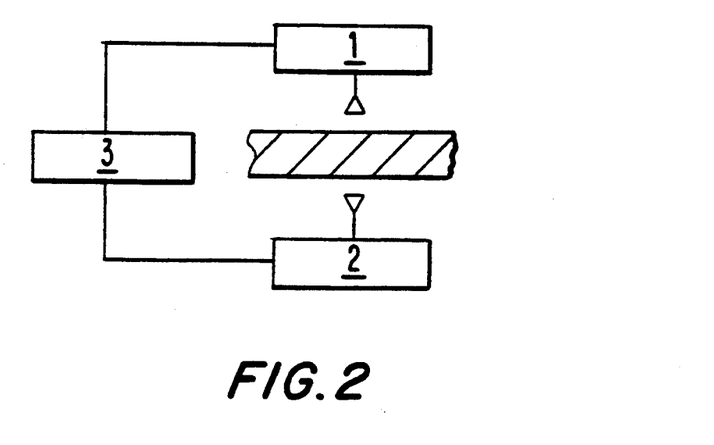
FIG. 2 illustrates the basic measurement set up for a first embodiment of the method of the invention.

Accordingly in one embodiment of the method of the invention for determining the moisture content of a material similar techniques of measuring the microwave transit time or the changes in it can be applied to a different kind of measurement situation shown in FIG. 2.

In the case of the invention the transit time is given as earlier stated by formula (2), because the microwave velocity in the material is decreased by an amount determined by the relative dielectric constant of the material. Instead of the constant velocity in radar case, now distance travelled by microwave in the material is constant and the microwave velocity changes as a function of the relative dielectric constant of the measured material. The dielectric constant of water is large compared with most other materials and thus the relative dielectric constant of the material (and with it the microwave velocity and the transit time through the material) changes as the moisture content of the material changes. This interdependence between the microwave velocity (or its relative changes) and the moisture content of the material can be measured with the method of the invention.

Figure 3:
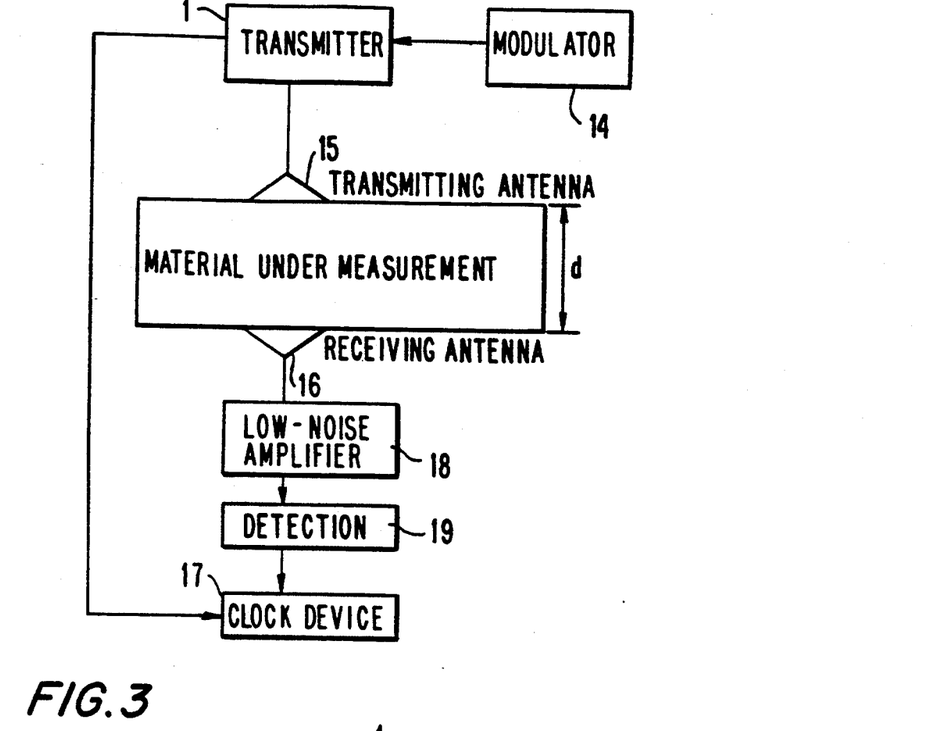
FIG. 3 illustrates the basic measurement set up for a second embodiment of the method of the invention, i.e. the transit time measurement setup.

In an embodiment of the method the change in the velocity of the microwave signal is determined by measuring the transit time of the microwave pulse, burst or pulse sequence, which has travelled through the material in a constant measuring gap. The transit time is measured directly, using a clock or clocks, as the time interval between the transmitted and the received microwave pulse, burst or pulse sequence. The basic configuration of this kind of measurement system is shown in FIG. 3., where a microwave pulse, pulse sequence or a narrow band microwave burst is produced and/or modulated and transmitted through the material at the measuring gap and received at the receiver. The transmitted pulse, pulses or burst starts and the received pulse, pulses or burst stops the clock or the clocks.

These techiques per se are commonly used in radar systems to determine distances in circumstances, where the medium (usually air) in which the microwave is propagating is homogeneous and stable (so that the wave propagates with a constant velocity) and are well documented e.g. by Skolnik, M. I.:Introduction to Radar Systems, 2nd Ed., New York. MacGraw-Hill 1980/.

After the transit time (t) is determined the microwave velocity (v) is then simply calculated from the formula (2):

$$v = d/t \quad (4)$$

where
  d=distance travelled by the microwave in the material
  t=measured transit time in the material Thus the changes in microwave velocity in the material under measurement can be measured, and the moisture content of the material can be determined on the basis of a known interdependence between the moisture content and the velocity changes in material.

The basic resolution of the transit time measurement is determined by the oscillator frequencies of the clock or clocks and their stability and the slew rates and the repeatabilities of the transmitted and received pulses, to which the clock start and stop signals are triggered. The shorter is the pulse (sharp rising edge) the better is the resolution. However, shorter pulses require a broader bandwidth and thus the received energy is smaller; therefore bursts and compressed pulses (chirps) are often used. /Skolnik M. I. . . . /.

Another technique is to use impulse radar technique, where an extremely short pulse is transmitted and the received signal is sampled only once for each transmitted pulse. By changing the time interval between the transmission and sampling, the whole received signal is gradually reconstructed. Thus an improvement of $1/\sqrt{n}$ on the signal to noise ratio of the received signal can be achieved (n is the amount of the samples). Of course the unstability of the measurement situation restricts the amount of the collected samples; if the velocity in the material changes rapidly and/or the dynamics of the velocity changes is wide, the error caused by the velocity changes during the sampling sequences will lead to inaccurate measurement results. /Baker, J. M., Clarke, J., Grant P. M. (eds.): IEE Proc., Vol. 135, Pt.F., No 4, August 1988 (Special Issue on Subsurface Radar) pp. 277-392./

The transit time measurement resolution of the clock system can further be improved with digital interpolation techniques where two or more stable oscillators are used (e.g. vernier or dual vernier methods), or analog interpolation techniques using e.g. charging and decharging of capacitors /Kostamovaara J., Myllylä R. Atime-to-Amplitude Converter with Constant Fraction Timing discriminators for Short Time Interval Measurements, Nucl. Instr. and Methods in Physics Research, A239, North-Holland, Amsterdam, 1985, pp 568-578./

The accuracy of the triggering of the start and stop signals to the rising edge of the pulse or the burst envelope can be improved by using techniques where the signals are triggered at the moment the pulse signal (or the burst envelope) reaches a predetermined constant fraction of its maximum amplitude/Kostamovaara J. et al . . . /.

Further accuracy can be achieved by using transmitted and received pulse sequences where the transit times of each pulse are determined either separately (and then averaged) or compared to a stable reference (like in digital interpolation techniques).

In an embodiment of the method the transmitter and the receiver are arranged on different sides relative to the material under measurement.

In an embodiment of the method the transmitter and the receiver are on the same side relative to the material to be measured and a reflector plate is provided on the opposite side to reflect the microwave signal proceeding from the transmitter to pass it to the receiver after it has travelled through the material.

In an embodiment of the method, the transit time of a continuous or intermittent pulse-type or pulse-sequence type microwave signal which has travelled through the material to be measured is determined by using correlation techniques, i.e. by transmitting wide-band noise or by modulating the microwave signal with random noise or random or pseudo random digital signals, and determining the transit time by the aid of the cross correlation function of the transmitted and the received signals.

The cross correlation function $R_{xy}(\partial)$ of the transmitted signal (or modulation) x(t) and received signal is given as follows:

$$R_{xy}(\partial) = \lim_{T \to \infty} \frac{1}{T} \int_0^T x(t) \, y(t + \partial) dt \quad (5)$$

where T=the observation time of the signals.

Theoretically the observation time should be infinite, but in practice a relatively short period is enough to achieve the accuracy needed in transit time measurement. This allows also the use of pseudo noise in the measurement: the noise sequence shall only be longer than the observation time for each single measurement result.

Because the received signal is basically the delayed transmitted signal (and some noise added) the transit time through the measured material can be determined from the cross correlation function as the delay value $\partial_m$ on which the cross correlation function reaches its maximum value /Bendat J. S., Piersol A. G.: Random Data: Analysis and Measurement Procedures, Wiley-Interscience, New York, 1971./

Figure 4:
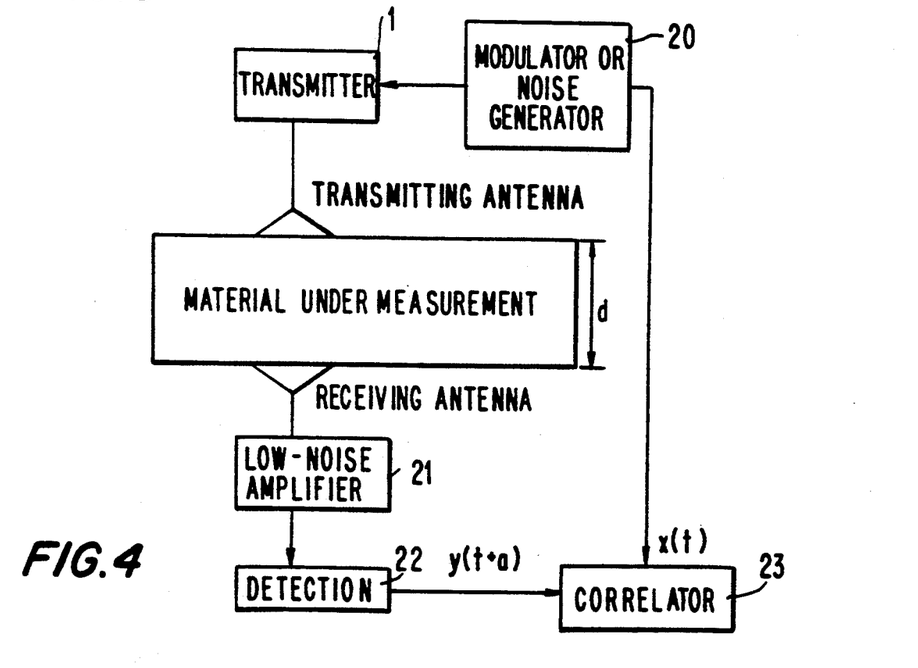
FIG. 4 illustrates the basic measurement set up for a third embodiment of the method of the invention, i.e. the correlation based measurement setup.

The main elements of the correlation measurement system are shown in FIG. 4, where the modulator modulates according to a random or pseudo random sequence the amplitude and/or phase of the transmitted continuous or intermittent signal or the amplitude of transmitted pulses and/or the time intervals between transmitted pulses. It's also possible to use random or pseudo random noise as the transmitted signal and then no special modulator is needed.

The received signal is amplified with a low-noise amplifier and demodulated (if needed) in the detection section. The cross correlation function (and the delay giving the maximum, i.e. the transit time through the material) of the transmitted modulation or noise and the detected modulation or noise is calculated at the correlator unit.

By modulating the transmitted and received signals with a pseudo random sequence and feeding the received modulation to a convolver together with an other pseudo random sequence that is identical but time-reversed the correlator function can be realized with a convolver (performing actually the autocorrelation function of the generated modulation) to determine the transit time through the material. /Wigger B., Knapp W., Basenfelder E.: A Microcomputer-Controlled Pseudo Noise modulated CW-Radar with SAW-Convolver for Signal Processing. 18th European Microwave Conference 12-16.9.1988, Stockholm, Sweden; Conference Proceedings pp. 844-848./

The velocity changes in the material can be determined as earlier stated by formula (4) and the moisture of the material under measurement can be determined on the basis of a known interdependence between moisture content of the material and the velocity changes in the material.

In an embodiment of the method, the change occurring in the velocity of the microwave signal when travelling through the material to be measured is determined with the aid of frequency modulation, whereby a microwave signal is produced, the frequency of the microwave signal is varied in accordance with a mathematical function from the lower limit $f_1$ to the upper limit $f_2$ of its frequency range and/or vice versa within a certain period of time T, the microwave signal is divided into a first component and a second component, the first component is transmitted through the material at the measuring point, the first component which has travelled through the material is mixed with the second component, an intermediate frequency signal $\Delta f$ corresponding to the delay is formed from the mixed signal thus obtained, and the moisture content of the material under measurement is determined from the signal $\Delta f$ on the basis of a known interdependence between the moisture content and the intermediate frequency signal $\Delta f$.

The intermediate frequency $\Delta f$ can also be calculated as follows:

$$\Delta f = B \cdot d \cdot ((\epsilon_r' + |\epsilon_r|)/2)^{\frac{1}{2}}/(T \cdot c) \quad (6)$$

where $B = f_2 - f_1$ = sweep width (width of the band within which the fequency varies)
$f_1$ = low limit of sweep band = lower frequency
$f_2$ = high limit of sweep band = higher frequency
$d$ = distance of advance of the microwave in the material
$\epsilon_r'$ = real part of the relative dielectric constant of the material
$\epsilon_r$ = relative dielectric constant of the material
$T$ = sweep time
$c$ = light velocity Table 1 shows typical intermediate frequency $\Delta f$ values for certain materials as obtained from the formula (6). The parameters employed are B=2 GHz, T=10 ms, d=30 cm and c=3·10⁸ m/s.

TABLE 1

| Calculated $\Delta f$ values for different materials. | | | |
|---|---|---|---|
| Material | $\epsilon_r'$ | $\epsilon_r''$ | $\Delta f$ (Hz) |
| Water | 80 | 5 | 1788 |

TABLE 1-continued

| Calculated $\Delta f$ values for different materials. | | | |
|---|---|---|---|
| Material | $\epsilon_r'$ | $\epsilon_r''$ | $\Delta f$ (Hz) |
| Wet wood | 23 | 2.5 | 959 |
| Dry wood | 3 | 0.1 | 346 |
| Air | 1 | 0 | 200 |

It can be seen from the table that the dielectric constant for water is high in comparison with the dielectric constants of the other materials. Therefore, the intermediate frequency is higher in the case of wet wood than in the case of dry wood.

The moisture content of a given material is determined from the frequency of the intermediate frequency signal $\Delta f$ either via calculation or by graphical means, provided that the interrelation between the moisture content of the material and the frequency of the intermediate frequency signal is known. This interrelation can be determined by performing several measurements using the method and apparatus of the invention on a material whose moisture content is known or is to be measured. Based on the measurement results, a function describing the interdependence of the two quantities is formed. This function is then utilized in measurements performed using the method and apparatus of the invention to determine or calculate the moisture content of materials. The interdependence function can be included in a computer program which computes the final value of the moisture content.

In an embodiment of the method, the frequency of the microwave signal is varied continuously and cyclically from the lower frequency $f_1$ to the upper frequency $f_2$ and then from the upper frequency $f_2$ to the lower frequency $f_1$.

In an embodiment of the method, the material to be measured consists of a stream of material such as wood chips, pulp fibers or a water suspension, e.g. chemical or mechanical wood pulp, which is passed through a measuring gap.

In an embodiment of the method, the determination of the moisture content is implemented as a continuous measuring process.

The apparatus of the invention comprises a transmitting device which transmits a microwave signal through the material to be measured, and a detecting device and a counting device which measure the change of velocity of the signal transmitted through the material and determine the moisture content of the material on the basis of a known interdependence of the change of velocity of the microwave signal in question and change of moisture content of the material.

In an embodiment of the apparatus of the invention, the transmitting device comprises an oscillator designed to produce a signal of a frequency in the microwave range and to vary the signal frequency from a lower frequency $f_1$ to an upper frequency $f_2$ and/or vice versa within a given period of time T in accordance with a mathematical function, an isolator designed to pass the signal in the oscillator circuit in only one direction, a directional coupler designed to divide the signal into a first component and a second component, and a transmitter (e.g. a transmitting antenna) designed to transmit the first signal component obtained from the directional coupler through the material to be measured; the detecting device comprises a receiver (e.g. a receiving antenna) designed to receive the first signal component after it has travelled through the material to be measured, a mixer provided with a first input gate, a second input gate and an output gate and designed to receive the first component from the receiver via its first input gate and the second component directly from the directional coupler via its second input gate and to mix the signals applied to the input gates, to produce from the signal thus formed an intermediate frequency signal corresponding to the delay and to output it through the output gate; and the counting device is designed to control the oscillator and to measure the frequency of the intermediate frequency signal obtained from the mixer output gate and to determine the moisture content value of the material under measurement from the intermediate frequency signal on the basis of a known interdependence of said signal and the moisture content.

In an embodiment of the apparatus, the transmitter and the receiver are arranged on different sides relative to the material under measurement.

In an embodiment of the apparatus, the transmitter and the receiver are on the same side relative to the material to be measured and a reflector plate is provided on the opposite side to reflect the microwave signal proceeding from the transmitter to pass it to the receiver after it has travelled through the material.

In an embodiment of the apparatus, the counting device is designed to control the oscillator in such a way that the frequency of the microwave signal is continuously varied from the lower frequency $f_1$ to the upper frequency $f_2$ and then from the upper frequency $f_2$ to the lower frequency $f_1$.

In an embodiment of the apparatus, the apparatus is provided with a first electric cable, a second electric cable and a third electric cable, of which the first electric cable conducts the microwave signal from the directional coupler to the second input gate of the mixer, the second electric cable conducts the signal from the directional coupler to the transmitter and the third electric cable conducts the signal from the receiver to the first input gate of the mixer, the lengths of the first, second and third electric cables being so chosen that the frequency of the intermediate frequency signal will be in a range that is technically easy to measure. The frequency of the intermediate frequency signal can also be adjusted to the desired level by altering the sweep width (B), the sweep time (T) or the distance (d) travelled by the microwave in the material under measurement.

In prior art, the so-called microwave frequency modulation (FM-CW) technique has been employed in short-distance radar applications e.g. for the measurement of the level of a surface or the thickness of ice. Such applications are described e.g. in the following publications: "An FM-Radar for Accurate Level Measurements", 9th European Microwave Conference, Brighton 1979, pp. 712-715, and Jakkula P., Ylinen P., Tiuri M.: "Measurement of Ice And Frost Thickness with an FM-CW Radar", 10th European Microwave Conference, Warsaw 1980.

In these previously known radar applications, the distance between the object of measurement and the radar transmitter/receiver varies, whereas the material, usually air, between the transmitter/receiver and the reflecting object remains unchanged as far as the microwave is concerned. According to the invention, the microwave frequency modulation technique (FM-CW technique) can be employed in a completely new area of application, i.e. measurement of the moisture content of a material, where it has never been applied before. The embodiment of the invention makes it possible to utilize all the advantages of the FM-CW technique in connection with the measurement of the moisture content of materials.

A further advantage of the invention is that the output signal to be measured permits easy processing or consists of a burst signal, the measurement of whose frequency is simple and easy and does not necessarily impose very high requirements on the electronics used in the apparatus.

In the following, the invention is described in detail by referring to the attached drawing, wherein

FIG. 1 illustrates a known basic radar measurement setup already disclosed above.

In FIG. 2 there is shown a basic measurement setup of the method of the invention. The system transmits a microwave signal through the material under measurement in a constant measuring gap d, whereupon it measures the change of velocity of the signal which has passed through the material and determines the moisture content of the material on the basis of a predetermined known interdependence between the change of velocity of the microwave signal in question and the change of moisture content of the material. The apparatus comprises a transmitting device 1, a detecting device 2 and a counting device 3. The transmitter 1 and the receiver 2 are here arranged on different sides relative to the material under measurement. The measurement of the change of velocity can be based on the transit time or noise correlation of a microwave pulse, burst or pulse sequence or frequency modulation.

In FIG. 3. there is shown the basic configuration of the measurement system, in which the change in the velocity of the microwave signal is determined by measuring the transit time of the microwave pulse, burst or pulse sequence, which has travelled through the material in a constant measuring gap d. The transit time is measured directly, using at least one clock, as a time interval between the transmitted and the received microwave pulse, burst or pulse sequence. A microwave pulse, pulse sequence or a narrow band microwave burst is first produced and/or modulated by transmitter 1 and/or modulator 14. Microwave pulse, burst or pulse sequence is transmitted by transmitting antenna 15 through the material and is received by the receiving antenna 16. The transmitted pulse, burst or pulse sequence starts the clock device 17 and the received and the received pulse, pulses or burst stops the clock device. The measurement setup further comprises a low-noise amplifier 18 for amplifying the signal, and a detection device 19.

From the measuring transit time (t) the microwave velocity (v) can be calculated from formula (4) stated above, when the distance (d) of the constant measuring gap is known. Thus the changes in microwave velocity in the material can be measured and the moisture content of the material can be determined on the basis of a known interdependence between the moisture content of the material and the velocity changes.

In FIG. 4 there are shown the main elements of the correlation measurement system for conducting a method, wherein the transit time of a continuous or intermittent pulse-type or pulse-sequence type microwave signal which has travelled through the material to be measured is determined by using correlation techniques, i.e. by transmitting wide-band noise or by modulating the microwave signal with random noise or random pseudo random digital signals, and determining the transit time by the aid of the cross correlation function of the transmitted and the received signals. The modulator 20 modulates according to a random or pseudo random sequence the amplitude and/or phase of the transmitted continuous or intermittent signal or the amplitude of transmitted pulses and/or the time intervals between transmitted pulses. It's also possible to use random or pseudo random noise as the transmitted signal and then no special modulator is needed.

The received signal is amplified with a low-noise amplifier 21 and demodulated (if needed) in the detection section 22. The cross correlation function (and the delay giving the maximum, i.e. the transit time through the material) of the transmitted modulation or noise and the detected modulation or noise is calculated at the correlator unit 23.

The velocity changes in the material can be determined as earlier stated in formula (4) and the moisture of the material under measurement can be determined on the basis of a known interdependence between moisture content of the material and the velocity changes in the material.

Figure 5:
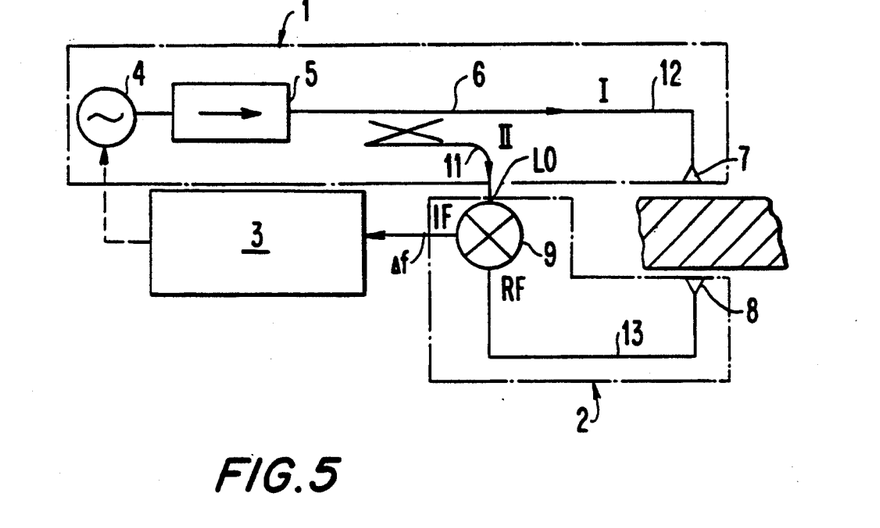
FIG. 5 illustrates the basic measurement set up for a third embodiment of the method of the invention, i.e. measurement setup employing microwave frequency modulation (FM-CW) technique.

In the measurement setup of FIG. 5, a microwave signal is transmitted through the material, whereupon, using frequency modulation, the system measures the change of velocity of the signal which has passed through the material and determines the moisture content of the material on the basis of a known interdependence between the change of velocity of the microwave signal and the change of moisture content of the material.

The apparatus comprises a transmitting device 1, a detecting device 2 and a counting device 3.

The transmitting device 1 consists of an oscillator 4, an isolator 5, a directional coupler 6 and a transmitter 7. The detecting device 2 consists of a receiver 8 and a mixer 9.

The oscillator 4 produces a microwave-frequency signal. Controlled by the counter 3, the oscillator changes the signal frequency in a linear fashion through a certain range of frequencies within a certain period of time. Thereupon the signal frequency is again changed linearly from the upper limit of the range to its lower limit. These cyclic variations are continued without interruption.

The isolator 5 takes care that the microwave signal is only allowed to travel in one direction in the oscillating circuit.

The directional coupler 6 divides the microwave signal into a first component I and a second component II. The first component I of the microwave signal is passed via the second electric cable 12 to the transmitter 7.

The transmitter 7 transmits the signal through the material under measurement.

The receiver 8 receives the microwave signal I which has travelled through the material under measurement. The transmitter and the receiver are placed on opposite sides of the material. On its way through the material, the signal I is retarded and delayed as compared to the second microwave signal component II, which is used as a reference quantity in the mixer 9.

The mixer comprises a first input gate RF, a second input gate LO and an output gate IF. The second input gate LO of the mixer is fed by the second signal component II, which is supplied directly from the directional coupler via cable 11. The first input gate RF of the mixer 9 is fed by the first signal component I, supplied by the receiver via cable 13.

In the mixer, the signals I and II applied to its input gates RF and LO are mixed. From the signal thus obtained, the mixer produces an intermediate frequency signal $\Delta f$, which is obtained from the output gate IF.

By suitably choosing the lengths of the electric cables 11, 12 and 13, the intermediate frequency signal $\Delta f$ corresponding to the delay is adjusted to a level allowing technically easy measurement.

The counting device 3 measures the frequency of the intermediate frequency signal $\Delta f$ obtained from the output gate IF of the mixer. The moisture content value of the material under measurement can be determined from this frequency on the basis of a known interdependence between the intermediate frequency signal $\Delta f$ and the moisture content. For a given material, this interdependence being known, the moisture content value is obtained either by calculation or by graphical means. The interdependence can be determined by performing several measurements with the method and apparatus of the invention on a material with known moisture content values. Based on the measurement results, a function describing the interdependence of the quantities is formed. This function is then utilized in the computation of the moisture content value of materials in measurements performed with the method and apparatus of the invention.

Figure 6A:
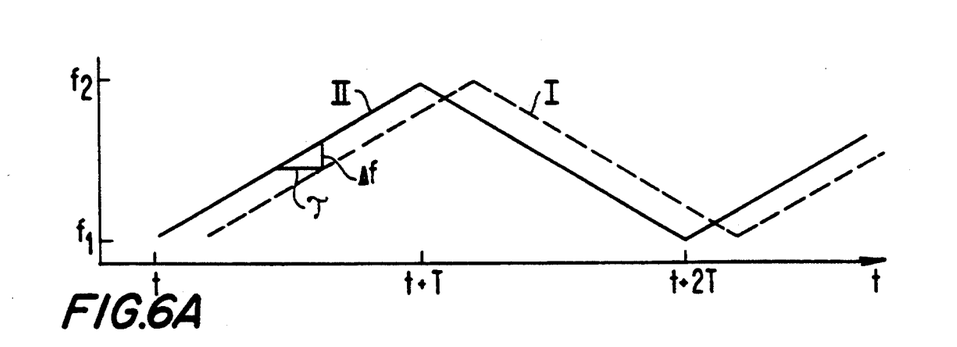
FIG. 6a shows the oscillator frequency and the mixer output signal of the apparatus in FIG. 5 as function of time.

FIG. 6a shows a graph representing the frequency of the microwave signals at the first input gate RF and at the second input gate LO of the mixer 9. The signal frequency changes from a lower frequency $f_1$ to a higher frequency $f_2$ during a period of time T, the slope of the change being constant. The signal I applied to the first input gate RF of the mixer is delayed by a length of time $\tau$ as compared to the signal II applied to the second input gate LO. The continuous line represents the signal II at the second input gate LO while the broken line represents the signal I at the first input gate RF. The time difference $\tau$ arises from the fact that the microwave signal is delayed on its way from the transmitter 7 to the receiver 8. From signals I and II, the mixer produces an intermediate frequency signal $\Delta f$, which is proportional to the moisture content of the material under measurement.

Figure 6B:
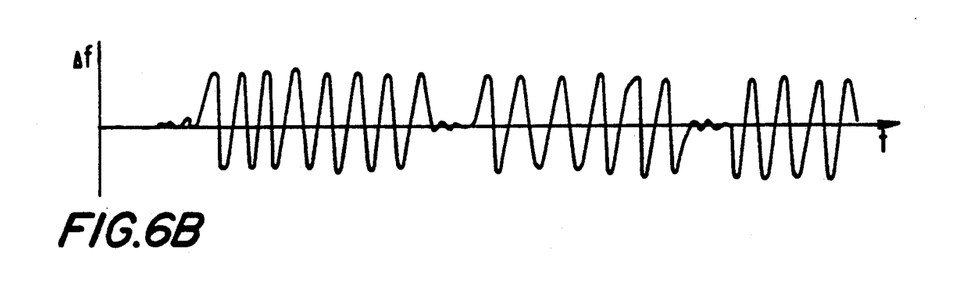
FIG. 6b shows the intermediate frequency $\Delta f$ of FIG. 6a as function of time.

The curve in FIG. 6b represents the amplitude of the intermediate frequency signal $\Delta f$ as a function of time.

Figure 7:
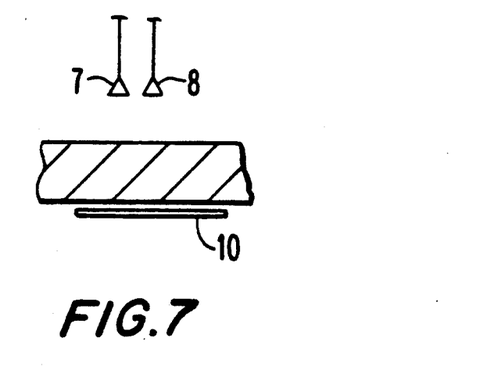
FIG. 7 shows a detail of a third embodiment of the apparatus of the invention.

FIG. 7 shows an embodiment in which the transmitter 7 and the receiver 8 are placed on the same side of the material under measurement, with a reflector plate 10 provided on the opposite side. The plate reflects the microwave signal transmitted by the transmitter 7 to the receiver 8.

Figure 8:
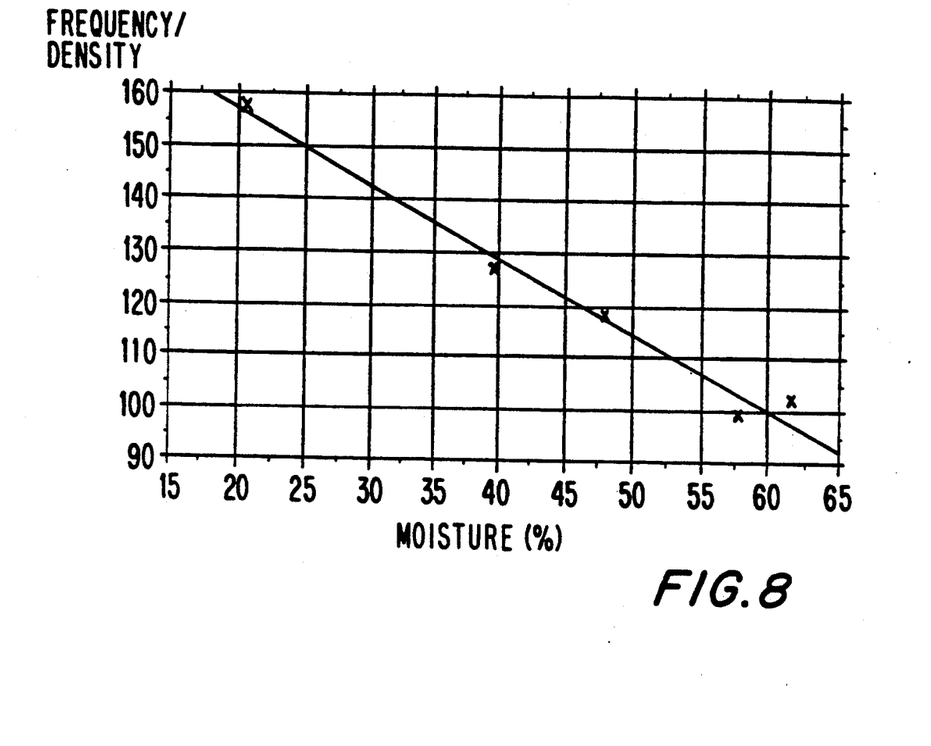
FIG. 8 shows an example of measurement results and a function determined from these results to determine the known interdependence between the intermediate frequency and the moisture of the wood chips.

FIG. 8 presents the results of measurements on wood chips. These measurements were performed by the method of the invention to determine the interdependence between the moisture content and the frequency of the intermediate frequency signal. The measurement parameters were B=0.9 GHz, T=11,1 ms and d=5 cm. The measurements were performed on wood chips with six different known moisture content values, so that the corresponding six frequencies of the intermediate frequency signal $\Delta f$ were obtained. Because the moisture content of wood chips was desired to be expressed in terms of percentages by weight at each measuring point, the frequency values were divided by the density of the sample under measurement, whereby the effects of different densities on the results were eliminated.

In the FIG. 8, the measurement results and the interdependence function obtained from them are presented in the form of a graph. The vertical axis represents the frequency of the intermediate frequency signal $\Delta f$ divided by the density of the material under measurement. The horizontal axis represents the moisture content of the wood chips in terms of percentages by weight.

Figure 9:
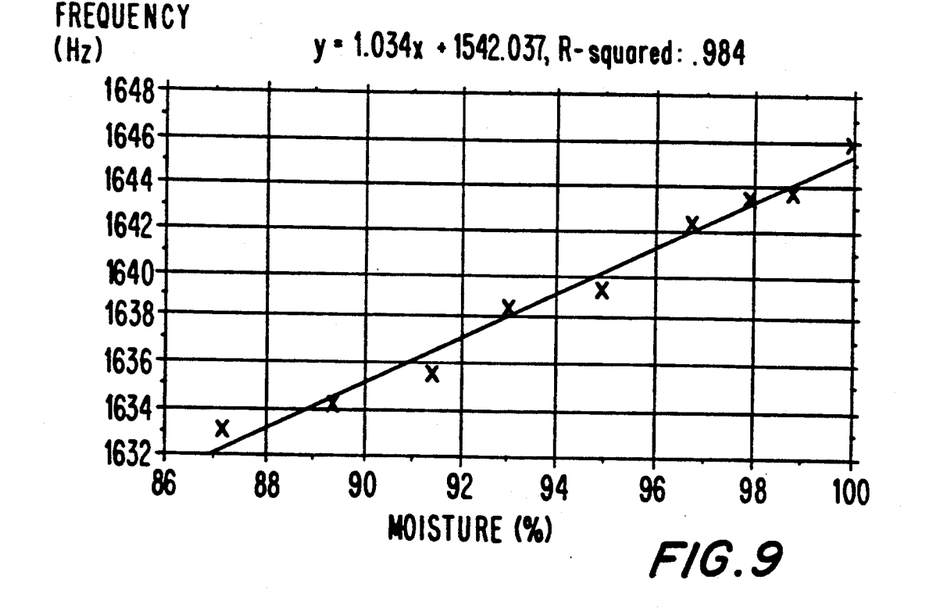
FIG. 9 shows an example of measurement results and a function determined from these results to determine the known interdependence between the intermediate frequency and the moisture of the pine pulp.

FIG. 9 presents the results of measurements on pine pulp. These measurements were performed by an embodiment of the method of the invention to determine the interdependence between the moisture content and the frequency of the intermediate frequency signal. The measurement parameters were B=0.9 GHz, T=11,1 ms and d=10 cm. The measurements were performed on pine pulp with nine different known moisture content values, so that the corresponding nine frequencies of the intermediate frequency signal $\Delta f$ were obtained. The moisture content of pine pulp is expressed in terms of percentages by weight at each measuring point.

In FIG. 9 the measurement results and the interdependence function obtained from them are presented in the form of a graph. The vertical axis represents the frequency of the intermediate frequency signal $\Delta f$. The horizontal axis represents the moisture content of the pine pulp in terms of percentages by weight.

The data for wood in Table 1 discloses the class on magnitude relating to solid wood and is therefore not comparable with the results of FIGS. 8 and measured on wood chips and pine pulp.

The invention is not restricted to the embodiment examples described above, but instead several variations are possible within the scope of the idea of the invention as defined in the following claims.

We claim:

1. Apparatus for determining the moisture content of a material, comprising a transmitting device which is arranged to transmit a microwave signal through the material to be measured, and a detecting device and a counting device which are arranged to measure the change of velocity of the signal transmitted through the material and to determine the moisture content of the material on the basis of said measured change and a predetermined known interdependence between the changes in the microwave signal velocity and the moisture content of the material, wherein the transmitting device comprises an oscillator designed to produce a signal of a frequency in the microwave range and to vary the signal frequency from a lower frequency $f_1$ to an upper frequency $f_2$ within a given period of time T in accordance with a mathematical function, an isolator designed to pass the signal in the oscillator circuit in only one direction, a directional coupler designed to divide the signal into a first component (I) and a second component (II), and a transmitter designed to transmit the first signal component obtained from the directional coupler through the material to be measured; that the detecting device comprises a receiver designed to receive the first signal component (I) after it has travelled through the material to be measured, a mixer provided with a first input gate (RF), a second input gate (LO) and an output gate (IF) and designed to receive the first component (I) from the receiver via its first input gate (RF) and the second component (II) directly from the directional coupler via its second input gate (LO) and to mix the signals applied to the input gates (LO) and (RF), to produce from the signal thus formed an intermediate frequency signal $\Delta f$ corresponding to the delay and to output it through the output gate (IF); and the counting device is designed to control the oscillator and to measure the frequency of the intermediate frequency signal $\Delta f$ obtained from the mixer output gate (IF) and to determine the moisture content value of the material under measurement from the intermediate frequency signal on the basis of a known interdependence of said signal $\Delta f$ and the moisture content.

2. Apparatus according to claim 1, comprising a clock device to determine the transit time of microwave signal travelled through the material in a constant measuring gap.

3. Apparatus according to claim 1, comprising a modulator device to modulate the microwave signal to be transmitted through the material.

4. Apparatus according to claim 1, wherein the transmitter and the receiver are located on different sides of the material under measurement.

5. Apparatus according to claim 1, wherein the transmitter and the receiver are on the same side relative to the material to be measured and a reflector plate is provided on the opposite side to reflect the transmitted microwave signal to the receiver.

6. Apparatus according to claim 1, wherein the counting device is designed to control the oscillator in such a way that the frequency of the microwave signal is continuously and cyclically varied from the lower frequency $f_1$ to the upper frequency $f_2$ and then from the upper frequency $f_2$ to the lower frequency $f_1$.

7. Apparatus according to claim 1, the apparatus is provided with a first electric cable, a second electric cable and a third electric cable, of which the first electric cable conducts the microwave signal from the directional coupler to the second input gate (LO) of the mixer, the second electric cable conducts the signal from the directional coupler to the transmitter and the third electric cable conducts the signal from the receiver to the first input gate (RF) of the mixer, the lengths of the first, second and third electric cables being such that the frequency of the intermediate frequency signal $\Delta f$ will be in a range that is technically easy to measure.

* * * * *